(12) United States Patent
Lamego

(10) Patent No.: US 8,761,850 B2
(45) Date of Patent: *Jun. 24, 2014

(54) REFLECTION-DETECTOR SENSOR POSITION INDICATOR

(71) Applicant: Masimo Corporation, Irvine, CA (US)

(72) Inventor: Marcelo Lamego, Coto De Caza, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/725,908

(22) Filed: Dec. 21, 2012

(65) Prior Publication Data

US 2013/0211264 A1 Aug. 15, 2013

Related U.S. Application Data

(63) Continuation of application No. 12/577,670, filed on Oct. 12, 2009, now Pat. No. 8,346,330.

(60) Provisional application No. 61/104,969, filed on Oct. 13, 2008.

(51) Int. Cl.
*A61B 5/00* (2006.01)

(52) U.S. Cl.
USPC .......................................................... 600/322

(58) Field of Classification Search
USPC .......................................................... 600/322
See application file for complete search history.

(56) References Cited

U.S. PATENT DOCUMENTS

| | | |
|---|---|---|
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |

(Continued)

*Primary Examiner* — Rodney Fuller
(74) *Attorney, Agent, or Firm* — Knobbe Martens Olson & Bear LLP

(57) ABSTRACT

A reflection-detector sensor position indicator comprises emitters that transmit light having a plurality of wavelengths. A detector outputs a sensor signal. At least one reflection detector outputs at least one sensor position signal. An attachment assembly attaches the emitters, the detector and the reflection detector onto a tissue site. A sensor-on condition indicates that the attachment assembly has positioned the emitters generally centered over a fingernail, the detector on a fingertip opposite the fingernail and the reflection detector over the fingernail. The sensor signal, in the sensor-on condition, is at least substantially responsive to the emitter transmitted light after attenuation by pulsatile blood flow perfused within a fingernail bed underneath the fingernail. The sensor position signal, in the sensor-on condition, is at least substantially responsive to the emitter transmitted light after reflection off of the fingernail.

19 Claims, 5 Drawing Sheets

(56) References Cited

U.S. PATENT DOCUMENTS

| | | | |
|---|---|---|---|
| 5,490,505 | A | 2/1996 | Diab et al. |
| 5,494,043 | A | 2/1996 | O'Sullivan et al. |
| 5,533,511 | A | 7/1996 | Kaspari et al. |
| 5,534,851 | A | 7/1996 | Russek |
| 5,561,275 | A | 10/1996 | Savage et al. |
| 5,562,002 | A | 10/1996 | Lalin |
| 5,588,427 | A | 12/1996 | Tien |
| 5,590,649 | A | 1/1997 | Caro et al. |
| 5,602,924 | A | 2/1997 | Durand et al. |
| 5,632,272 | A | 5/1997 | Diab et al. |
| 5,638,816 | A | 6/1997 | Kiani-Azarbayjany et al. |
| 5,638,818 | A | 6/1997 | Diab et al. |
| 5,645,440 | A | 7/1997 | Tobler et al. |
| 5,685,299 | A | 11/1997 | Diab et al. |
| D393,830 | S | 4/1998 | Tobler et al. |
| 5,743,262 | A | 4/1998 | Lepper, Jr. et al. |
| 5,758,644 | A | 6/1998 | Diab et al. |
| 5,760,910 | A | 6/1998 | Lepper, Jr. et al. |
| 5,769,785 | A | 6/1998 | Diab et al. |
| 5,782,757 | A | 7/1998 | Diab et al. |
| 5,785,659 | A | 7/1998 | Caro et al. |
| 5,791,347 | A | 8/1998 | Flaherty et al. |
| 5,810,734 | A | 9/1998 | Caro et al. |
| 5,823,950 | A | 10/1998 | Diab et al. |
| 5,830,131 | A | 11/1998 | Caro et al. |
| 5,833,618 | A | 11/1998 | Caro et al. |
| 5,860,919 | A | 1/1999 | Kiani-Azarbayjany et al. |
| 5,890,929 | A | 4/1999 | Mills et al. |
| 5,904,654 | A | 5/1999 | Wohltmann et al. |
| 5,919,134 | A | 7/1999 | Diab |
| 5,934,925 | A | 8/1999 | Tobler et al. |
| 5,940,182 | A | 8/1999 | Lepper, Jr. et al. |
| 5,995,855 | A | 11/1999 | Kiani et al. |
| 5,997,343 | A | 12/1999 | Mills et al. |
| 6,002,952 | A | 12/1999 | Diab et al. |
| 6,011,986 | A | 1/2000 | Diab et al. |
| 6,027,452 | A | 2/2000 | Flaherty et al. |
| 6,036,642 | A | 3/2000 | Diab et al. |
| 6,045,509 | A | 4/2000 | Caro et al. |
| 6,067,462 | A | 5/2000 | Diab et al. |
| 6,081,735 | A | 6/2000 | Diab et al. |
| 6,088,607 | A | 7/2000 | Diab et al. |
| 6,110,522 | A | 8/2000 | Lepper, Jr. et al. |
| 6,124,597 | A | 9/2000 | Shehada |
| 6,128,521 | A | 10/2000 | Marro et al. |
| 6,129,675 | A | 10/2000 | Jay |
| 6,144,868 | A | 11/2000 | Parker |
| 6,151,516 | A | 11/2000 | Kiani-Azarbayjany et al. |
| 6,152,754 | A | 11/2000 | Gerhardt et al. |
| 6,157,850 | A | 12/2000 | Diab et al. |
| 6,165,005 | A | 12/2000 | Mills et al. |
| 6,184,521 | B1 | 2/2001 | Coffin, IV et al. |
| 6,206,830 | B1 | 3/2001 | Diab et al. |
| 6,229,856 | B1 | 5/2001 | Diab et al. |
| 6,232,609 | B1 | 5/2001 | Snyder et al. |
| 6,236,872 | B1 | 5/2001 | Diab et al. |
| 6,241,683 | B1 | 6/2001 | Macklem et al. |
| 6,253,097 | B1 | 6/2001 | Aronow et al. |
| 6,256,523 | B1 | 7/2001 | Diab et al. |
| 6,263,222 | B1 | 7/2001 | Diab et al. |
| 6,278,522 | B1 | 8/2001 | Lepper, Jr. et al. |
| 6,280,213 | B1 | 8/2001 | Tobler et al. |
| 6,285,896 | B1 | 9/2001 | Tobler et al. |
| 6,301,493 | B1 | 10/2001 | Marro et al. |
| 6,317,627 | B1 | 11/2001 | Ennen et al. |
| 6,321,100 | B1 | 11/2001 | Parker |
| 6,325,761 | B1 | 12/2001 | Jay |
| 6,334,065 | B1 | 12/2001 | Al-Ali et al. |
| 6,343,224 | B1 | 1/2002 | Parker |
| 6,349,228 | B1 | 2/2002 | Kiani et al. |
| 6,360,114 | B1 | 3/2002 | Diab et al. |
| 6,368,283 | B1 | 4/2002 | Xu et al. |
| 6,371,921 | B1 | 4/2002 | Caro et al. |
| 6,377,829 | B1 | 4/2002 | Al-Ali |
| 6,388,240 | B2 | 5/2002 | Schulz et al. |
| 6,397,091 | B2 | 5/2002 | Diab et al. |
| 6,430,437 | B1 | 8/2002 | Marro |
| 6,430,525 | B1 | 8/2002 | Weber et al. |
| 6,463,311 | B1 | 10/2002 | Diab |
| 6,470,199 | B1 | 10/2002 | Kopotic et al. |
| 6,501,975 | B2 | 12/2002 | Diab et al. |
| 6,505,059 | B1 | 1/2003 | Kollias et al. |
| 6,515,273 | B2 | 2/2003 | Al-Ali |
| 6,519,487 | B1 | 2/2003 | Parker |
| 6,525,386 | B1 | 2/2003 | Mills et al. |
| 6,526,300 | B1 | 2/2003 | Kiani et al. |
| 6,541,756 | B2 | 4/2003 | Schulz et al. |
| 6,542,764 | B1 | 4/2003 | Al-Ali et al. |
| 6,580,086 | B1 | 6/2003 | Schulz et al. |
| 6,584,336 | B1 | 6/2003 | Ali et al. |
| 6,595,316 | B2 | 7/2003 | Cybulski et al. |
| 6,597,932 | B2 | 7/2003 | Tian et al. |
| 6,597,933 | B2 | 7/2003 | Kiani et al. |
| 6,606,511 | B1 | 8/2003 | Ali et al. |
| 6,632,181 | B2 | 10/2003 | Flaherty et al. |
| 6,639,668 | B1 | 10/2003 | Trepagnier |
| 6,640,116 | B2 | 10/2003 | Diab |
| 6,643,530 | B2 | 11/2003 | Diab et al. |
| 6,650,917 | B2 | 11/2003 | Diab et al. |
| 6,654,624 | B2 | 11/2003 | Diab et al. |
| 6,658,276 | B2 | 12/2003 | Kianl et al. |
| 6,661,161 | B1 | 12/2003 | Lanzo et al. |
| 6,671,531 | B2 | 12/2003 | Al-Ali et al. |
| 6,678,543 | B2 | 1/2004 | Diab et al. |
| 6,684,090 | B2 | 1/2004 | Ali et al. |
| 6,684,091 | B2 | 1/2004 | Parker |
| 6,697,656 | B1 | 2/2004 | Al-Ali |
| 6,697,657 | B1 | 2/2004 | Shehada et al. |
| 6,697,658 | B2 | 2/2004 | Al-Ali |
| RE38,476 | E | 3/2004 | Diab et al. |
| 6,699,194 | B1 | 3/2004 | Diab et al. |
| 6,714,804 | B2 | 3/2004 | Al-Ali et al. |
| RE38,492 | E | 4/2004 | Diab et al. |
| 6,721,582 | B2 | 4/2004 | Trepagnier et al. |
| 6,721,585 | B1 | 4/2004 | Parker |
| 6,725,075 | B2 | 4/2004 | Al-Ali |
| 6,728,560 | B2 | 4/2004 | Kollias et al. |
| 6,735,459 | B2 | 5/2004 | Parker |
| 6,745,060 | B2 | 6/2004 | Diab et al. |
| 6,760,607 | B2 | 7/2004 | Al-All |
| 6,770,028 | B1 | 8/2004 | Ali et al. |
| 6,771,994 | B2 | 8/2004 | Kiani et al. |
| 6,792,300 | B1 | 9/2004 | Diab et al. |
| 6,813,511 | B2 | 11/2004 | Diab et al. |
| 6,816,741 | B2 | 11/2004 | Diab |
| 6,822,564 | B2 | 11/2004 | Al-Ali |
| 6,826,419 | B2 | 11/2004 | Diab et al. |
| 6,830,711 | B2 | 12/2004 | Mills et al. |
| 6,850,787 | B2 | 2/2005 | Weber et al. |
| 6,850,788 | B2 | 2/2005 | Al-Ali |
| 6,852,083 | B2 | 2/2005 | Caro et al. |
| 6,861,639 | B2 | 3/2005 | Al-Ali |
| 6,898,452 | B2 | 5/2005 | Al-Ali et al. |
| 6,920,345 | B2 | 7/2005 | Al-Ali et al. |
| 6,931,268 | B1 | 8/2005 | Kiani-Azarbayjany et al. |
| 6,934,570 | B2 | 8/2005 | Kiani et al. |
| 6,939,305 | B2 | 9/2005 | Flaherty et al. |
| 6,943,348 | B1 | 9/2005 | Coffin, IV |
| 6,950,687 | B2 | 9/2005 | Al-Ali |
| 6,961,598 | B2 | 11/2005 | Diab |
| 6,970,792 | B1 | 11/2005 | Diab |
| 6,979,812 | B2 | 12/2005 | Al-Ali |
| 6,985,764 | B2 | 1/2006 | Mason et al. |
| 6,993,371 | B2 | 1/2006 | Kiani et al. |
| 6,996,427 | B2 | 2/2006 | Ali et al. |
| 6,999,904 | B2 | 2/2006 | Weber et al. |
| 7,003,338 | B2 | 2/2006 | Weber et al. |
| 7,003,339 | B2 | 2/2006 | Diab et al. |
| 7,015,451 | B2 | 3/2006 | Dalke et al. |
| 7,024,233 | B2 | 4/2006 | Ali et al. |
| 7,027,849 | B2 | 4/2006 | Al-Ali |
| 7,030,749 | B2 | 4/2006 | Al-Ali |
| 7,039,449 | B2 | 5/2006 | Al-Ali |
| 7,041,060 | B2 | 5/2006 | Flaherty et al. |

(56) References Cited

U.S. PATENT DOCUMENTS

| | | | |
|---|---|---|---|
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty et al. |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,255,026 B1 | 8/2012 | Al-Ali |
| 8,255,028 B2 | 8/2012 | Al-Ali et al. |
| 8,260,577 B2 | 9/2012 | Weber et al. |
| 8,274,360 B2 | 9/2012 | Sampath et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 * | 1/2013 | Lamego ............ 600/322 |
| 8,353,842 B2 | 1/2013 | Al-Ali et al. |
| 8,355,766 B2 | 1/2013 | MacNeish, III et al. |
| 8,359,080 B2 | 1/2013 | Diab et al. |

(56) References Cited

U.S. PATENT DOCUMENTS

| | | |
|---|---|---|
| 8,364,223 B2 | 1/2013 | Al-Ali et al. |
| 8,364,226 B2 | 1/2013 | Diab et al. |
| 8,385,995 B2 | 2/2013 | Al-ali et al. |
| 8,399,822 B2 | 3/2013 | Al-Ali |
| 8,401,602 B2 | 3/2013 | Kiani |
| 2003/0139656 A1 | 7/2003 | Kiani et al. |
| 2006/0009685 A1 | 1/2006 | Finarov et al. |
| 2006/0178580 A1 | 8/2006 | Nakamura et al. |
| 2006/0220881 A1 | 10/2006 | Al-Ali et al. |
| 2008/0122803 A1 | 5/2008 | Izadi et al. |
| 2009/0018417 A1* | 1/2009 | Wang .............................. 600/316 |
| 2009/0027358 A1* | 1/2009 | Hosono ......................... 345/175 |

* cited by examiner

REFLECTION-DETECTOR SENSOR POSITION INDICATOR

CROSS-REFERENCE TO RELATED APPLICATIONS

The present application is a continuation of U.S. patent application Ser. No. 12/577,670, filed Oct. 12, 2009, titled Reflection-Detector Sensor Position Indicator, which claims priority benefit under 35 U.S.C. §119(e) to U.S. Provisional Patent Application Ser. No. 61/104,969, filed Oct. 13, 2008, titled Reflection-Detector Sensor Position Indicator, hereby incorporated by reference herein.

BACKGROUND OF THE INVENTION

Pulse oximetry is a technique that utilizes a noninvasive sensor to determine a person's oxygen status. An optical sensor used in pulse oximetry has light emitting diodes (LEDs) that transmit optical radiation of red and infrared wavelengths into a tissue site. A detector in the sensor responds to the intensity of the optical radiation after attenuation by pulsatile arterial blood flowing within the tissue site. Based on this response, a processor determines measurements for $SpO_2$ and pulse rate among other parameters. Pulse oximeters capable of reading through motion induced noise are available from Masimo Corporation ("Masimo") of Irvine, Calif. Moreover, portable and other pulse oximeters capable of reading through motion induced noise are disclosed in at least U.S. Pat. Nos. 6,770,028, 6,658,276, 6,157,850, 6,002,952, 5,769,785 and 5,758,644, which are owned by Masimo and are incorporated by reference herein. Corresponding low noise optical sensors are also available from Masimo and are disclosed in at least U.S. Pat. Nos. 6,985,764, 6,813,511, 6,792,300, 6,256,523, 6,088,607, 5,782,757 and 5,638,818. Such reading through motion pulse oximeters and low noise sensors have gained rapid acceptance in a wide variety of medical applications, including surgical wards, intensive care and neonatal units, general wards, home care, physical training, and virtually all types of monitoring scenarios. Moreover, pulse oximeters capable of reading through motion induced noise and low noise optical sensors including LNOP® disposable, reusable and/or multi-site sensors and Radical®, Rad-5™, Rad-8™, Rad-9™, PPO+™ monitors are also available from Masimo.

Further, noninvasive blood parameter monitors capable of measuring parameters in addition to $SpO_2$, such as HbCO, HbMet and Hbt, and corresponding multiple wavelength optical sensors are also available from Masimo. Noninvasive blood parameter monitors and corresponding multiple wavelength optical sensors are described in at least U.S. patent application Ser. No. 11/367,013, filed Mar. 1, 2006, titled Multiple Wavelength Sensor Emitters and U.S. patent application Ser. No. 11/366,208, filed Mar. 1, 2006, titled Noninvasive Multi-Parameter Patient Monitor, both assigned to Masimo Laboratories, Irvine, Calif. (Masimo Labs) and both incorporated by reference herein. Moreover, multiple parameter monitors and multiple wavelength sensors including Rad-57™ and Radical-7™ monitors and Rainbow™ Rainbow™-brand adhesive and reusable sensors are available from Masimo. MS- and MX-brand processor boards are also available from Masimo.

SUMMARY OF THE INVENTION

Problems arise if a pulse oximeter or other blood parameter monitor is connected to an optical sensor that is not properly positioned on a tissue site or becomes partially or completely dislodged from a patient, a so-called "probe off" condition. When an optical sensor is properly positioned on a tissue site, the detector only receives LED emitted light that has propagated via the tissue site to the detector after tissue scattering and absorption. Thus, the AC detector signal that results accurately reflects the differential absorption of constituents in the pulsatile arterial blood, as described above. If a sensor is off a tissue site or is mis-positioned on the tissue site, the detector may directly receive LED emitted light, i.e. light that has not propagated through any tissue. Despite a probe-off condition, a blood parameter monitor may continue to detect an AC signal, which can be induced at the detector by other than pulsatile arterial attenuation of LED emitted light. Small patient movements, vibrations, air flow or other perturbations may cause the pathlength between the LEDs and detector to vary, resulting in an AC detector signal that can be mistakenly interpreted by the monitor as due to pulsatile arterial blood. Further, ambient light may reach the detector, and any modulation of the ambient light due to AC power, power fluctuations, moving objects, such as a fan, among other perturbations can also be mistaken as a pulsatile arterial signal. Probe-off errors are serious because a blood parameter monitor may still display a normal measurement, potentially leading to critical missed events, such as a patient desaturation.

An aspect of an optical sensor comprises emitters that transmit light having a plurality of wavelengths. A detector outputs a sensor signal. At least one reflection detector outputs at least one sensor position signal. An attachment assembly attaches the emitters, the detector and the reflection detector onto a tissue site. A sensor-on condition indicates that the attachment assembly has positioned the emitters generally centered over a fingernail, the detector on a fingertip opposite the fingernail and the reflection detector over the fingernail. The sensor signal, in the sensor-on condition, is at least substantially responsive to the emitter transmitted light after attenuation by pulsatile blood flow perfused within a fingernail bed underneath the fingernail. The sensor position signal, in the sensor-on condition, is at least substantially responsive to the emitter transmitted light after reflection off of the fingernail.

In various embodiments, the optical sensor has a first reflection detector and a second reflection detector that generate a first sensor position signal and a second sensor position signal in response to reflected light from the emitters. The first reflection detector and the second reflection detector are positioned on opposite sides of the emitters. The magnitudes of the first sensor position signal and the second sensor position signal each have values within a sensor-on range of values during a sensor-on condition. At least one of the magnitudes of the first sensor position signal and the second sensor position signal have values within a sensor mis-positioned range of values when an attachment assembly positions the emitters partially off the center of the fingernail. The magnitudes of the first sensor position signal and the second sensor position signal each have values within a sensor-off range of values when the attachment assembly positions the emitters substantially off of the fingernail. The magnitude of the first sensor position signal has values in a mis-positioned range of values and the magnitude of the second position signal having values in a sensor-on range of values when the attachment assembly positions the emitters in a sensor over-positioned condition partially off-center of the fingernail and proximate the fingertip. The magnitude of the first sensor position signal has values in a sensor-on range of values and the magnitude of the second sensor position signal has values in a mis-positioned range of values when the attachment assembly positions the emitters off-center of the fingernail and distal the fingertip in a sensor under-positioned condition.

An aspect of a sensor position indicator comprises activating emitters with an emitter activation signal so as to transmit light, receiving a sensor position signal from a reflection detector responsive to reflections of the transmitted light, and indicating a sensor attachment condition in response to the sensor position signal. In various embodiments, the magnitude of the sensor position signal is determined with respect to at least one of a sensor-on range of values and a sensor mis-positioned range of values. A second sensor position signal is received from a second reflection detector responsive to reflections of the transmitted light. The magnitude of the second sensor position signal is determined with respect to at least one of a sensor-on range of values and a sensor mis-positioned range of values. The magnitude of the sensor position signal is compared to the magnitude of the second sensor position signal so as to determine at least one of a sensor over-positioned range of values, a sensor under-positioned range of values and a sensor-off range of values. A monitor display graphically depicts at least multiple ones of a sensor-on condition, a sensor-off condition, a sensor over-positioned condition and a sensor under-positioned condition.

An aspect of a physiological measurement system comprises a sensor having an attachment assembly configured to position emitters over a fingernail and to position a detector on a fingertip opposite the fingernail so that the emitters are positioned to transmit multiple wavelength light into the fingernail and so that the detector is positioned to detect the transmitted light after attenuation by pulsatile blood flow perfused within a fingernail bed underneath the fingernail and generate a sensor signal responsive to the intensity of the detected light. A second detector incorporated within the sensor generates a sensor position signal responsive to the position of the emitters over the fingernail. A physiological monitor is in communications with the sensor so as to drive the emitters, receive the corresponding sensor signal from the detector, and receive the corresponding sensor position signal from the second detector. The physiological monitor derives physiological parameters from the sensor signal and derives a sensor position indicator from the sensor position signal.

In various embodiments, the physiological measurement system comprises a third detector incorporated within the sensor that generates a second sensor position signal responsive to the position of the emitters over the fingernail. The physiological monitor derives multiple ones of a sensor-on condition, a sensor-off condition and a sensor mis-positioned condition from the sensor position signal and the second sensor position signal. The physiological monitor derives a sensor under-positioned condition and a sensor over-positioned condition from the sensor position signals. The physiological monitor generates a display that depicts the position of a finger relative to the sensor so as to visually indicate multiple ones of a sensor-on condition, a sensor-off condition, a sensor under-positioned condition and a sensor over-positioned condition. The physiological measurement system comprises an audible indicator of multiple ones of a sensor-on condition, a sensor-off condition, a sensor under-positioned condition and a sensor over-positioned condition.

A further aspect of a sensor position indicator comprises an emitter means for transmitting light into a tissue site so as to determine physiological parameters derived from detection of the light after attenuation by pulsatile blood flow within the tissue site, a reflection detection means for generating a sensor position signal responsive to reflections of the transmitted light, and a processor means for determining a sensor position condition from the magnitude of the sensor position signal.

An embodiment further comprises a display means for indicating the sensor position condition. The reflection detection means may comprise a first reflection detector means and a second reflection detector means located relative to the emitter means so as to determine a sensor over-positioned condition, a sensor under-positioned condition and a sensor-off condition. The processor means may comprise a calculation means for determining a first signal magnitude from the first reflection detector means and a second signal magnitude from the second signal magnitude. The process means may further comprises a comparator means for comparing the first signal magnitude and the second signal magnitude to each other and to ranges of sensor position values.

DETAILED DESCRIPTION OF THE PREFERRED EMBODIMENTS

Figure 1:
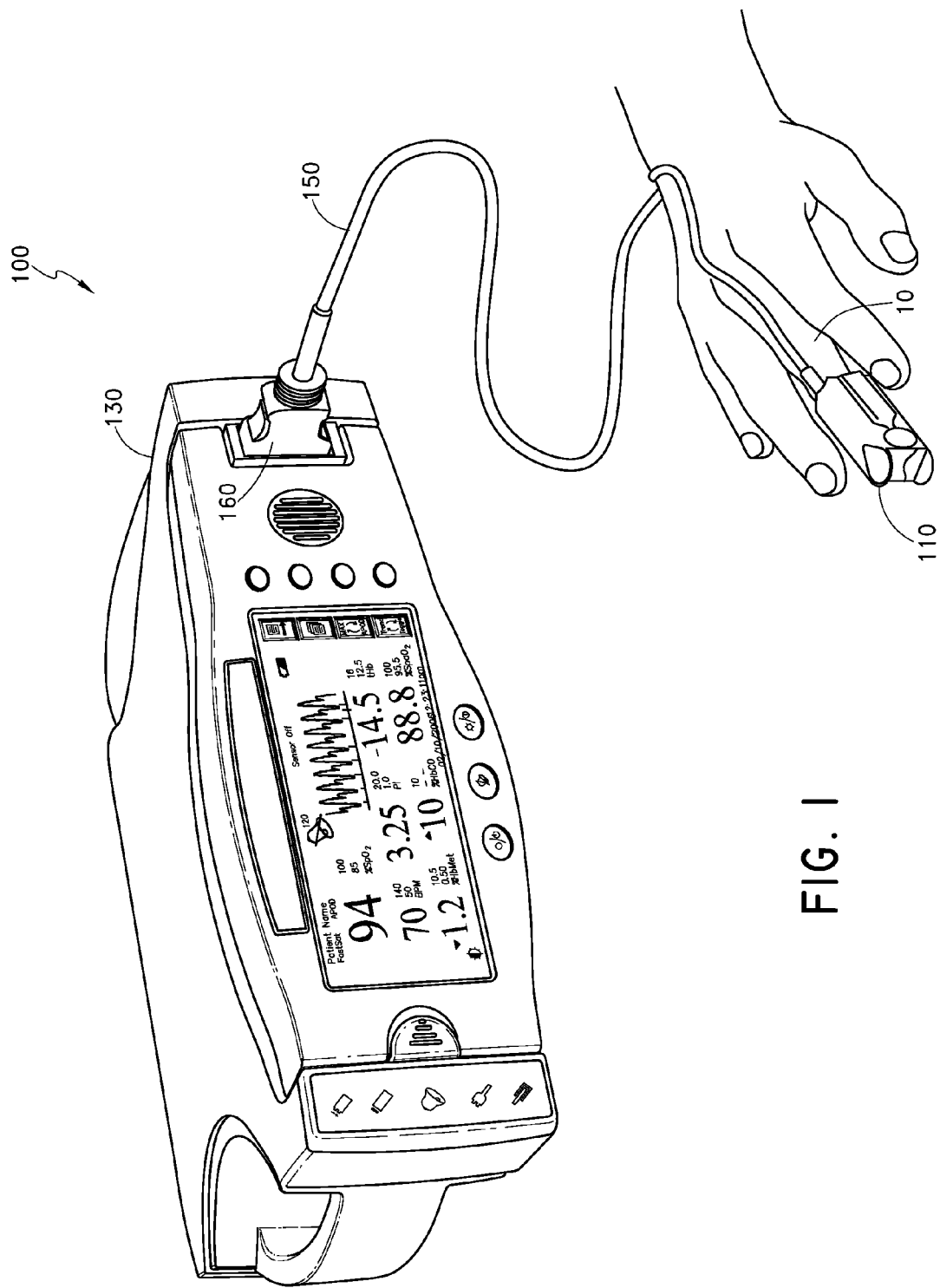
FIG. 1 is a perspective illustration of a physiological measurement system utilizing a reflection-detector sensor position indicator.
Figure 2:
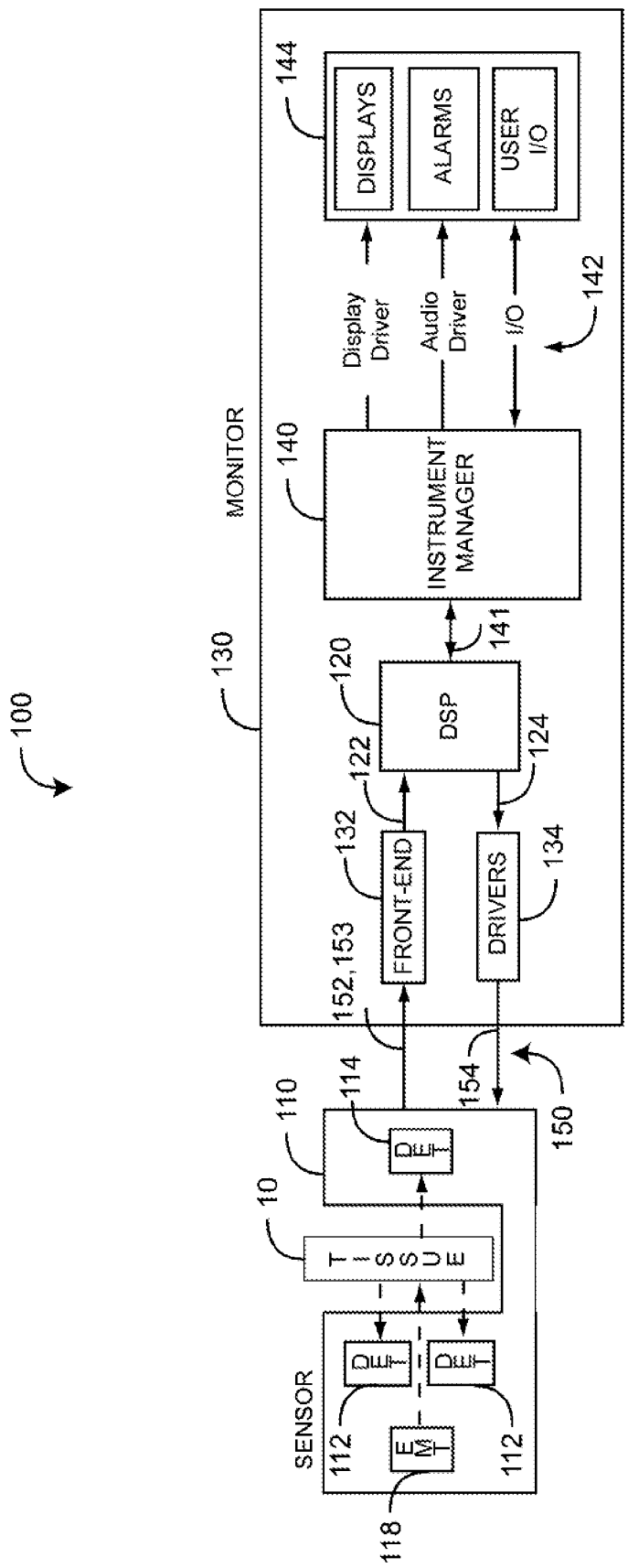
FIG. 2 is a block diagram of a physiological measurement system utilizing a reflection-detector sensor position indicator.

FIGS. 1-2 illustrate a physiological measurement system 100 which measures blood constituents and related parameters, such as oxygen saturation, pulse rate, perfusion index (PI), pleth variability index (PVI™), HbCO, HbMet and Hbt, to name a few. The physiological measurement system 100 includes an optical sensor 110 applied to a tissue site 10, a physiological monitor 130 and a cable 150 that physically and electrically connects the sensor 110 to the monitor 130. Advantageously, the physiological measurement system 100 also utilizes a sensor position indicator responsive to improper placement of the sensor 110 on a finger or other tissue site 10, as described in detail below.

As shown in FIGS. 1-2, the monitor 130 communicates with the sensor 110 to receive one or more sensor signals indicative of one or more physiological parameters. In particular, a digital signal processor (DSP) 120 outputs digital control signals 124 to drivers 134 and inputs digital data 122 from the front-end 132. The drivers 134 convert the digital control signals 124 into analog drive signals 154 capable of driving sensor emitters 118, which transmit optical radiation having multiple wavelengths into a tissue site 10. A primary detector 114 responds to the intensity of the optical radiation after attenuation by pulsatile blood flow within the tissue site 10 and generates a corresponding sensor signal 152. The front-end 132 converts the analog sensor signal 152 into the input digital data 122 to the DSP 120. The DSP 120 comprises any of a wide variety of data and signal processors capable of executing programs for determining physiological parameters from input data. The instrument manager 140, which may comprise one or more microcontrollers, has communications 141 with the DSP 120, such as to monitor activity of the DSP 138 and download calculated parameters. The instrument manager 140 also has communications 142 with displays, alarms and user input/output (I/O) 144. In an embodiment, a display 144 depicts the position of a finger relative to the sensor according to any of a sensor on, sensor off and sensor mis-positioned condition.

Also shown in FIG. 2, in an embodiment, a sensor position indicator incorporates one or more reflection detectors 112 located inside the sensor 110. The reflection detectors 112 generate sensor position signals 153 that are responsive to the emitter 118 being properly positioned over a fingernail bed and the corresponding high reflectivity of a fingernail. In this manner, a sensor position signal 153 that are weakly or non-responsive to the emitter 118 are indicative of a sensor-off or a sensor mis-positioned condition, as described in further detail with respect to FIGS. 3A-B, below.

Figure 3A:
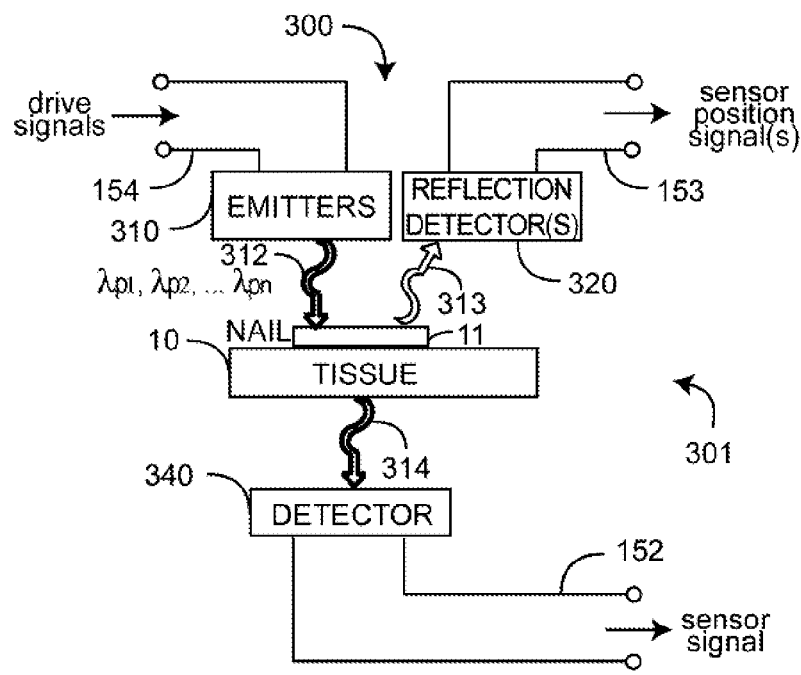
FIGS. 3A-B are general block diagrams of a reflection-detector sensor position indicator illustrating sensor-on and sensor-off conditions, respectively.
Figure 3B:
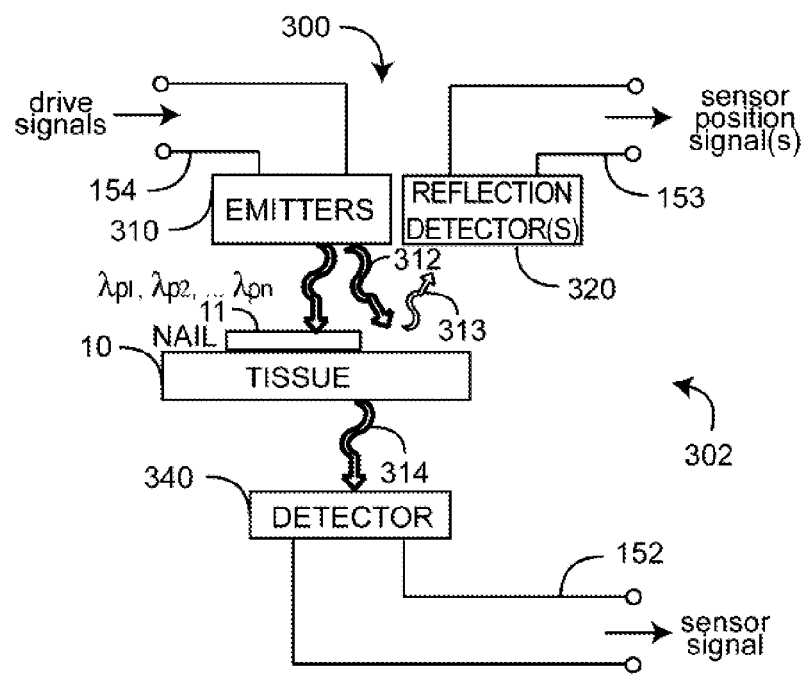

FIGS. 3A-B illustrate a sensor 300 having one or more reflection detectors 320 configured for sensor position indication. The sensor 300 has emitters 310 capable of transmitting light having wavelengths ($\lambda_p$) 312 into a tissue site 10 in response to a drive signals 154. A detector 340 detects the transmitted light 312 after attenuation by the tissue site 10 and outputs a sensor signal 152 responsive to the tissue-attenuated light 314. The sensor signal 152 is indicative of at least one physiological parameter corresponding to the tissue site 10. Advantageously, the sensor 300 has at least one reflection detector 320 that detects reflected light 313 from a nail 11 and outputs a sensor position signal 153 responsive to the nail-reflected light 313. The sensor position signal 153 is indicative of sensor position, as described in further detail below. A monitor 130 (FIG. 2) is in communications with the sensor 300 via the drive signals 154 and the corresponding sensor signal 152 and sensor position signal 153.

As shown in FIG. 3A, a sensor-on condition 301 is where the tissue site 10 is properly placed relative to the detector 340 so that accurate physiological measurements can be made. In particular, an emitter 310 is placed so as to substantially illuminate a blood-perfused nail bed underneath a fingernail 11. For example, in a sensor-on condition 301, the reflection detector 320 receives emitted light 312 after reflection 313 from the relatively reflective surface of a fingernail 11 and generates a relatively large AC and DC sensor position signal 153 accordingly.

As shown in FIG. 3B, a sensor mis-positioned condition or a sensor-off condition 302 is where the tissue site 10 is displaced relative to the emitters 310, so that the emitters do not illuminate a substantial portion of a nail bed. For example, in a sensor mis-positioned condition or a sensor-off condition 302, the reflection detector 320 receives emitted light 312 after reflection 313 from a relatively non-reflective surface, such as skin surrounding the fingernail 11 and generates a relatively small AC and DC secondary sensor signal 152 accordingly. Various embodiments of a sensor position indicator utilizing a reflection detector is described with respect to FIGS. 4-5, below.

FIGS. 4A-D illustrate a reflection detector sensor 400 having emitters 410, such as emitters 310 (FIGS. 3A-B), a detector 420, such as a detector 340 (FIGS. 3A-B) and at least one reflection detector 430, 440, such as reflection detectors 320 (FIGS. 3A-B). The reflection detector sensor 400 has an insertion end 12 that accepts a fingertip or, generally, insertion of a tissue site. Advantageously, the reflection detectors 430, 440 are capable of distinguishing a sensor-on condition 405, a sensor under-positioned condition 406, a sensor over-positioned condition 407 and a sensor-off condition 408.

Figure 4A:
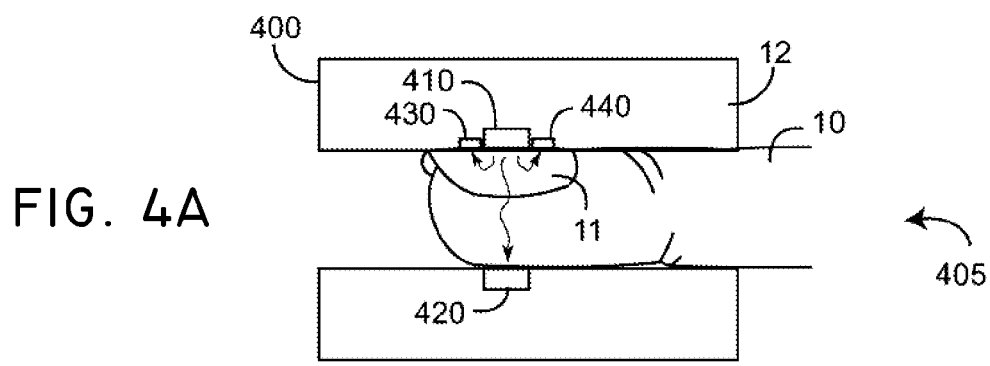
FIGS. 4A-D are side view illustrations of a reflection-detector sensor position indicator illustrating sensor-on, sensor under-positioned, sensor over-positioned and sensor-off conditions, respectively.

As shown in FIG. 4A, in a sensor-on condition 405, a fingertip is placed the proper distance into the sensor from the insertion end 12 so that both reflection detectors 430, 440 detect the increased reflectivity of emitted light from the emitters 410 positioned squarely over the fingernail 11. In the sensor-on condition 405, the emitters 410 transmit light directly into the blood-perfused nail bed underneath the fingernail 11.

Figure 4B:
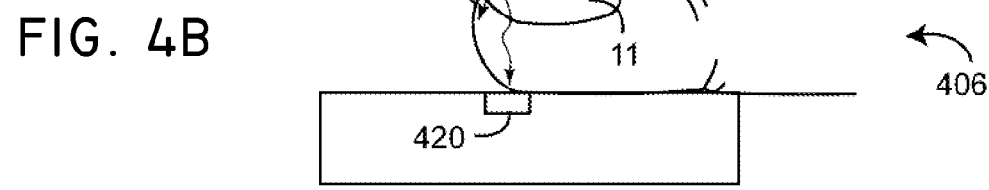

As shown in FIG. 4B, in a sensor under-positioned condition 406, a finger 10 is not inserted far enough into the reflection-detector sensor 400. As a result, the emitters 410 are positioned at least partially away from the center of the fingernail 11 and, accordingly, are only able to partially transmit light into the fingernail bed. Further, a first reflection detector 430 distal the insertion end 12 is also distal the center of the fingernail so that it detects a reduced light intensity compared to a second reflection detector 440 proximate the insertion end 12.

Figure 4C:
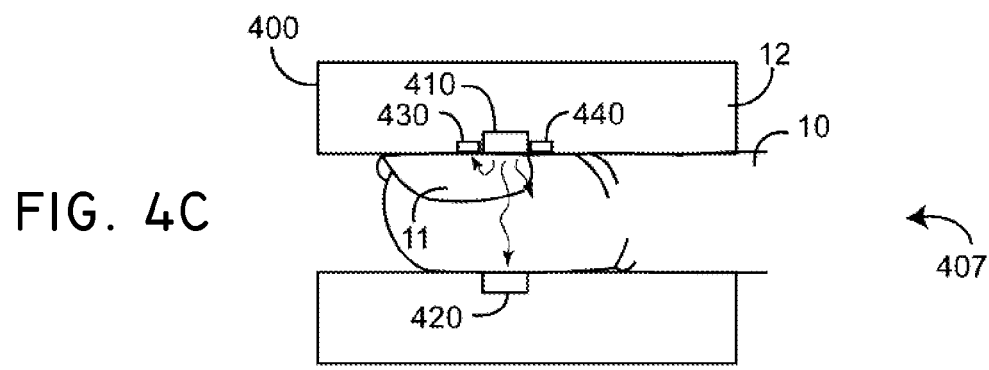

As shown in FIG. 4C, in a sensor over-positioned condition 407, a finger 10 is inserted too far into the reflection-detector sensor 400. Similar to the sensor under-positioned condition 406, this results in the emitters 410 being positioned at least partially away from the center of the fingernail 11 and only partially able to transmit light into the fingernail bed. Further, a second reflection detector 440 proximate the insertion end 12 is distal the center of the fingernail 11 so that it detects a reduced light intensity compared to a first reflection detector 430 distal the insertion end 12.

Figure 4D:
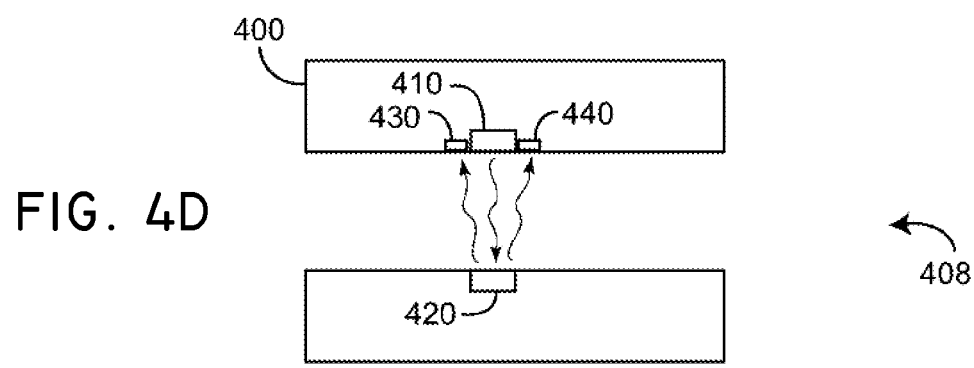

As shown in FIG. 4D, in a sensor-off condition 408, the sensor 400 is significantly misplaced on a fingertip or completely removed from a finger 10. Accordingly, the reflection detectors 430, 440 both detect the reduced reflectivity of the emitters 410 positioned over an air gap and the opposite side of the sensor 400 compared with emitters 410 positioned over a fingernail 11 as in the sensor-on condition 405 (FIG. 4A).

Figure 5A:
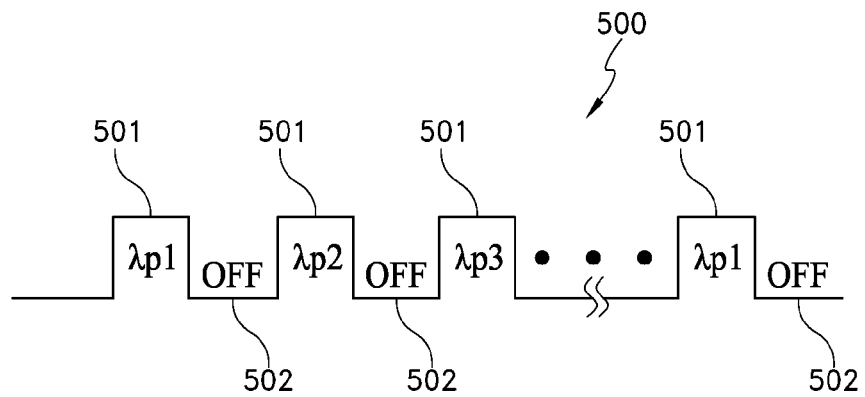
FIGS. 5A-C are timing diagrams for a reflection-detector sensor position indicator illustrating emitter drive signals and corresponding reflection-detector output signals related to high-reflectivity and low-reflectivity surfaces, respectively.
Figure 5B:
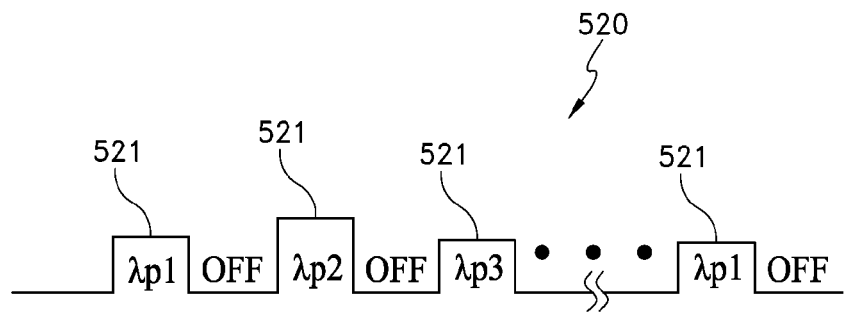
Figure 5C:
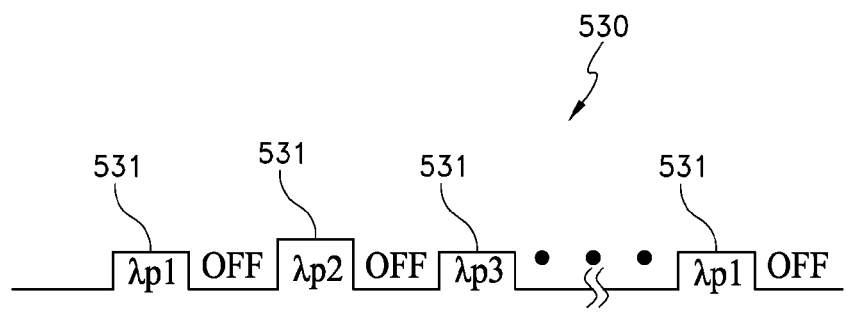

FIGS. 5A-C illustrate timing diagrams 500-530 for emitter drive currents, such as from monitor drive signals 154 (FIGS. 3A-B) and corresponding reflection detector response currents, such as to generate sensor position signals 153 (FIGS. 3A-B). As shown in FIG. 5A, emitter drive currents 500 have drive periods 501 and off periods 502 for each emitted wavelength $\lambda_{pi}$ FIG. 5B illustrates a relatively large reflection detector response 520 corresponding to a high-reflectivity surface. Specifically, the on periods 521 corresponding to the emitter drive periods 501 (FIG. 5A) indicate that emitted light is reflected off a nail surface and received by a reflection detector 430, 440 (FIG. 4A). FIG. 5C illustrates a relatively small reflection detector response 530 corresponding to a low-reflectivity surface. Specifically, the on periods 531 corresponding to the emitter drive periods 501 (FIG. 5A) indicate that emitted light is reflected off a relatively low reflectivity skin-surface or sensor-surface and received by a reflection detector 430, 440 (FIG. 4A). A monitor 130 (FIG. 2) determines which reflection detectors 430, 440 (FIG. 4A) receive the emitted light off of a high-reflectivity surface or a low-reflectivity surface so as to distinguish sensor-on, sensor under-positioned, sensor over-positioned and sensor-off conditions, as described with respect to FIGS. 4A-D, above.

A reflection-detector sensor position indicator has been disclosed in detail in connection with various embodiments. These embodiments are disclosed by way of examples only and are not to limit the scope of the claims that follow. One of ordinary skill in art will appreciate many variations and modifications.

What is claimed is:

1. An optical sensor configured to provide an indication of a physiological parameter comprising:
   a plurality of emitters that transmit light having a plurality of wavelengths;
   a detector that outputs a sensor signal, the sensor signal responsive to the emitter transmitted light after attenuation by pulsatile blood flow perfused within a fingernail bed underneath the fingernail, the detector positioned on a different side of the fingernail bed from the plurality of emitters; and
   at least one reflection detector that outputs at least one sensor position signal, the reflection detector positioned on the same side of the fingernail bed as the plurality of emitters.

2. The optical sensor according to claim 1 further comprising:
   a first reflection detector and a second reflection detector generating a first sensor position signal and a second sensor position signal in response to reflected light from the emitters;
   the first reflection detector and the second reflection detector positioned on opposite sides of the emitters; and
   the magnitudes of the first sensor position signal and the second sensor position signal each having values within a sensor-on range of values during a sensor-on condition.

3. The optical sensor according to claim 2 further comprising:
   a sensor mis-positioned condition in which an attachment assembly positions the emitters partially off a center of the fingernail bed; and
   at least one of the magnitudes of the first sensor position signal and the second sensor position signal having values within a sensor mis-positioned range of values.

4. The optical sensor according to claim 2 further comprising:
   a sensor-off condition in which an attachment assembly positions the emitters substantially off of the fingernail bed;
   the magnitudes of the first sensor position signal and the second sensor position signal each having values within a sensor-off range of values.

5. The optical sensor according to claim 2 further comprising:
   a sensor under-positioned condition in which an attachment assembly positions the emitters partially off-center of the fingernail bed and proximate the fingertip;
   the magnitude of the first sensor position signal having values in a mis-positioned range of values; and
   the magnitude of the second position signal having values in a sensor-on range of values.

6. The optical sensor according to claim 2 further comprising:
   a sensor over-positioned condition in which an attachment assembly positions the emitters off-center of the fingernail bed and distal a fingertip associated with the fingernail bed;
   the magnitude of the first sensor position signal having values in a sensor-on range of values; and
   the magnitude of the second sensor position signal having values in a mis-positioned range of values.

7. A sensor position indicating method comprising:
   activating a plurality of emitters with an emitter activation signal so as to transmit light;
   receiving a sensor position signal from a reflection detector responsive to reflections of the transmitted light;
   receiving a light attenuation signal from a detector that is responsive to the emitter transmitted light after attenuation by pulsatile blood flow, the detector positioned on an different side of a living tissue measurement site from the plurality of emitters; and
   indicating a tissue placement condition in response to the sensor position signal.

8. The sensor position indicating method according to claim 7 further comprising determining the magnitude of the sensor position signal with respect to at least one of a sensor-on range of values and a sensor mis-positioned range of values.

9. The sensor position indicating method according to claim 8 further comprising:
   receiving a second sensor position signal from a second reflection detector responsive to reflections of the transmitted light; and
   determining the magnitude of the second sensor position signal with respect to at least one of a sensor-on range of values and a sensor mis-positioned range of values.

10. The sensor position indicating method according to claim 9 further comprising comparing the magnitude of the sensor position signal to the magnitude of the second sensor position signal so as to determine at least one of a sensor over-positioned range of values, a sensor under-positioned range of values and a sensor-off range of values.

11. The sensor position indicating method according to claim 10 further comprising graphically depicting on a monitor display at least multiple ones of a sensor-on condition, a sensor-off condition, a sensor over-positioned condition and a sensor under-positioned condition.

12. A physiological measurement system comprising:
   a sensor having an attachment assembly configured to position emitters over a living tissue measurement site and to position a detector on a different side of the measurement site so that the emitters are positioned to transmit multiple wavelength light into the measurement site and so that the detector is positioned to detect the transmitted light after attenuation by pulsatile blood flow perfused within the tissue site and generate a sensor signal responsive to the intensity of the detected light;
   a second detector incorporated within the sensor that generates a sensor position signal responsive to the position of the emitters with respect to the tissue site; and
   an audible indicator of multiple ones of a sensor-on condition, a sensor-off condition, a sensor under-positioned condition and a sensor over-positioned condition.

13. The physiological measurement system according to claim 12 further comprising:
   a third detector incorporated within the sensor that generates a second sensor position signal responsive to the position of the emitters over the measurement site.

14. The physiological measurement system according to claim 12 wherein:
   the physiological monitor derives a sensor under-positioned condition and a sensor over-positioned condition from the sensor position signals.

15. A sensor position indicator comprising:
   an emitter means for transmitting light into a tissue site;
   a detector means, positioned on a different side of the tissue site from the emitter means, for detecting light attenuated by the tissue site configured to be used to determine physiological parameters;
   a reflection detection means, positioned on the same side of the tissue site as the emitter means, for generating a sensor position signal responsive to reflections of the transmitted light; and a processor means for determining a sensor position condition from the magnitude of the sensor position signal.

16. The sensor position indicator according to claim 15 further comprising a display means for indicating the sensor position condition.

17. The sensor position indicator according to claim 15 wherein the reflection detection means comprises a first reflection detector means and a second reflection detector means located relative to the emitter means so as to determine a sensor over-positioned condition, a sensor under-positioned condition and a sensor-off condition.

18. The sensor position indicator according to claim 15 wherein the processor means comprises a calculation means for determining a first signal magnitude from the first reflection detector means and a second signal magnitude from the second signal magnitude.

19. The sensor position indicator according to claim 18 wherein the process means further comprises a comparator means for comparing the first signal magnitude and the second signal magnitude to each other and to ranges of sensor position values.

\* \* \* \* \*